(12) United States Patent
Rovetta et al.

(10) Patent No.: US 6,416,485 B1
(45) Date of Patent: Jul. 9, 2002

(54) INSTRUMENTAL MEASUREMENT OF THE NEURO-PSYCHO-PHYSICAL STATE OF A PERSON

(75) Inventors: Alberto Rovetta, Milano; Antonino Cuce', Crema; Marco Dalessandri, Ripalta Arpina; Davide Platania, Crema; Gian Guido Rizzotto, Civate, all of (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 60 days.

(21) Appl. No.: 09/702,912

(22) Filed: Oct. 27, 2000

(30) Foreign Application Priority Data

Oct. 28, 1999 (EP) .......................... 99830679
Apr. 7, 2000 (EP) .......................... 00201271

(51) Int. Cl.$^7$ .......................... A61B 5/103; A61B 5/117
(52) U.S. Cl. .......................... 600/595; 600/587
(58) Field of Search .......................... 600/300, 587, 600/595; 73/379.01, 379.02, 379.03, 379.04

(56) References Cited

U.S. PATENT DOCUMENTS 4,199,987 A  4/1980 Bauers et al. .......... 73/379.04
4,949,729 A * 8/1990 Haski .......................... 600/587
5,573,011 A * 11/1996 Felsing .......................... 600/595
5,573,013 A * 11/1996 Conlan .......................... 600/595
5,885,231 A * 3/1999 Cramer et al. .......... 600/595

FOREIGN PATENT DOCUMENTS

FR          2671713       7/1992       ............ A61B/5/11

* cited by examiner

Primary Examiner—Kevin Shaver
Assistant Examiner—Charles Marmar, II
(74) Attorney, Agent, or Firm—Lisa K. Jorgenson; Allen, Dyer, Doppelt, Milbrath & Gilchrist, P.A.

(57) ABSTRACT

A method of assessing the neuro-psycho-physical condition of a person includes acquiring, by a self-contained hand held instrumentation, reaction times, execution times and ergometric data of actions performed by the person carrying out a certain test. This test includes processing the time data and the ergometric data for calculating the power exerted in performing each action. Data on the reaction time and the exerted power is processed on the basis of certain software to produce information on the neuro-psycho-physical condition. The ergometric data and reaction time data are processed by a fuzzy logic processor. The hand held instrument may optionally include also motion and voice articulation classifiers.

39 Claims, 10 Drawing Sheets

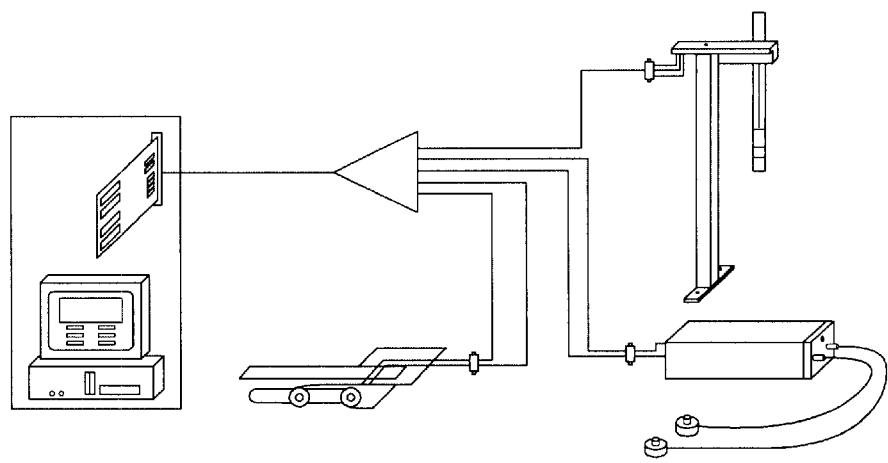
FIG. 1.
PRIOR ART
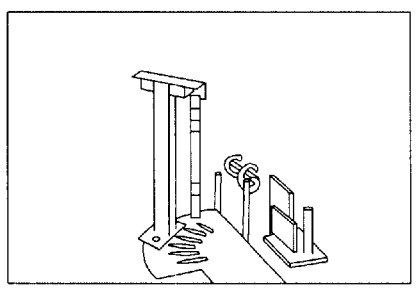 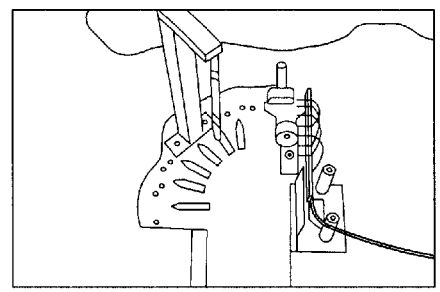
FIG. 2.　　　　　　　　FIG. 3.
PRIOR ART　　　　　　PRIOR ART
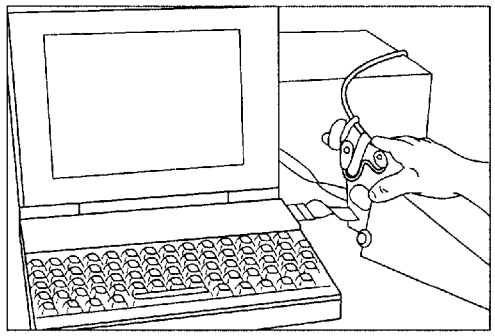 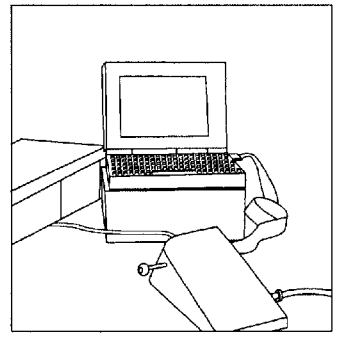
FIG. 4.　　　　　　　　FIG. 5.
PRIOR ART　　　　　　PRIOR ART

INSTRUMENTAL MEASUREMENT OF THE NEURO-PSYCHO-PHYSICAL STATE OF A PERSON

FIELD OF THE INVENTION

The present invention relates in general to instrument systems for data acquisition, processing and evaluation for determining the neuro-psycho-physical state of a person. In particular, the present invention relates to a portable system for automatically determining the neuro-psycho-physical condition of patients affected by Paralysis Agitans (Parkinson's disease) and other similar type diseases.

BACKGROUND OF THE INVENTION

Parkinson's disease is a degenerative process of the central nervous system having a slow and progressive evolution. The anatomopological alteration includes damage of neurons having dopaminergical melaninic content, which is located in the cerebral trunk, with consequent reactive gliosys. Biochemical studies have demonstrated a dysfunction of the dopaminergical nigrostriatal system. Dopamine is a chemical medium by which neurons communicate among each other. Parkinson's disease exhibits rigidity (muscular hypertonicity), akinesys, and tremor.

Rigidity opposes passive stretching of the muscles with a constant resistance that yields movement. There is a prevalence of the hypertonicity of the flexor muscles and this explains the general posture of the patient: head and trunk forward leaning, arms slightly flexed, and at the hand level the thumb is flexed.

Acinesy is characterized by slowness and global reduction of voluntary mobility. The patient is inexpressive. There is a reduction of the pendular movements of the arms during walking and a person with Parkinson's disease has difficulties in executing alternate movements rapidly, like drumming with fingers, making moving shadows, and making flex-extensions of the first finger. In addition, handwriting tends to become small (micrography), speech tends to become monotonic with sudden accelerations.

Acinesy may have a unilateral beginning and predominance. Sometimes following an emotion, acinesy may suddenly disappear. This demonstrates that the neural structures for the movements are not inhibited, but their stimulation requires exceptional excitations.

Tremor is present at rest. It generally disappears when executing a voluntary movement, during sleep, and following a complete muscle relaxation. Emotions, stress, and concentration efforts stimulate tremor. Moreover, tremor of an upper limb may appear while exerting the other upper limb. Generally, it is a regular tremor with a rhythm of 4–8 cycles per second. It starts at the extremity of the upper limb with alternate movements of flexal-extension of the fingers and of the thumb (similar to the gesture of counting coins). Other symptoms are hypersalivation, hypersweating, and orthostatic hypotension while osteotendineous reflexes are normal.

In view of the evolutive character of the disease, methods for multiparametric assessment have been developed to provide an incruent instrumental indication of the neuro-psycho-physical state of a patient.

Multiparametric measurement of reaction times of an individual may be useful for establishing the state of neuro-psycho-physical health of a generally healthy person. This is in addition to aiding diagnosis and monitoring of the progress of Parkinson's disease. Multiparametric measurement is an excellent way of discriminating alterations of reactive parameters due to other causes than the disease itself, such as the ingestion/consumption of alcoholics, drugs, psycho-pharmaceutical products or other substances that have an effect on the reactive and coordination capacities of a person.

A known method of diagnostic testing is the multiparametric measurement of the times of vocal reaction, which is described in the book "Neurologie del comportamento (errori e correzione del controllo cerebrate)" by P. Pinelli, Ed. Ambrosiana, 1997.

The person is instructed to provide a certain reply to a given signal. The reply may include pressing a push button as fast as possible. Stimulations of various types occur from time to time, and the person must press on a keyboard a certain key associated to the particular stimulation. To restrict the period of attention of the person, an alerting signal may precede the stimulation assignment.

The stimulation may be visual or audio. It may be a displayed test, an acronym, a word, or a phrase. The stimulations are presented in casual succession and the person may be called to pronounce the displayed expressions loudly to implement what is referred to as a reading reaction. Other stimulations may be figures, of which the person must pronounce the name, implementing what is normally called a reaction to figure identification.

In all these cases, every sound expressed is recorded as such through a microphone. In all the reactions, the time between the display of the stimulation to the instant when the answer begins is defined as the time of reaction. Since individual reaction time is normally slightly different from the preceding one and from the successive one in a series of reactions tests, the average and the relative standard deviation for a certain number of reaction tests to the same type of stimulation are calculated and recorded.

Typically, to obtain a significant average value about 10–12 reactions tests may be necessary. The brain functions statically and such a mode of functioning implies oscillations of the times and characters of performances. It is therefore important to detect also the duration of the reply beside its correctness, both in relationship to the stimulation as well as a sequence of movements. Accuracy of the reply is also important and in case of verbal replies, even sound frequencies may be analyzed.

The utility of measuring also the duration of the reply depends from the fact that it reflects the sequence of the various movements that are notably commanded through very complex neural controls. Another method of test is described in the article: "Advances In Occupational Medicine And Rehabilitation" by F. Ceriani et al.

This method rests on two tests. One of immediate reading and one of retarded reading. In the immediate reading, the patient is requested to pronounce the word immediately as displayed on the screen. In the retarded reading test, the patient must wait for an execution command given by a series of asterisks that appear above and below the displayed word. In a first test the reaction time is measured. In a second test the time for executing the central cerebral processing is assessed, and only after the time taken by the articulation. The patient is requested to translate a conceptual structure in a linguistic structure highlighting all the aspects, such as the grammatical coding of a message, the coding of a phonetic diagram and of a diagram of the articulation of each word.

In the last phase a phonetic diagram based on the muscle reaction, on the larynx and supra-larynx respiration, and on the oromandibular system is effected. In this way the synchronization between articulation and time necessary to express the words may be verified.

A different approach of instrumental testing includes a bioengineering system of acquisition and production of data on the movement of a finger. This system was developed by Professor Alberto Rovetta, and is based on the following protocols: fast movement, uncontrolled movement, controlled movement, and movement with virtual control.

Referring to fast movement, the person must touch from an initial reference point with the first finger of the hand a target as fast as possible. This is designed to measure the impressed force while in parallel other parameters are detected, among which include the angular position and the velocity of the finger and the reaction time.

Referring to uncontrolled movement, the person must make the same movement of the preceding protocol without watching their own finger. Instead, the person must do it by memorizing the procedure learned during the execution of the preceding protocol of fast movement, thus activating the person's working memory. For a controlled movement, the person must control the speed of execution in such a way that by observing the target, he may have to slow down his movement before hitting it.

Referring to movement with virtual control, the person is to follow on a graphic display the virtual image of his finger and at the moment in which his finger touches the real target, the virtual finger on the display changes color. This indicates the reaching of the target and the end of the test.

The bioengineering system is formed by the following. An exoskeleton mounted on a stand for establishing the position of the finger to be placed inside a glove like receptacle; potentiometers in correspondence to the joints flanges of the finger for detecting their movements; surface electrodes which through a bichannel probe provide a signal to an electromyograph; and instrumentation for measuring the force exerted on a target lamina on which strain gages are mounted.

The exoskeleton is supported by a common desktop PC with a ISA/EISA data acquisition card (model PC LPM 16 National Instruments) and by a software developed in Microsoft Visual C++ with development environment libraries LabWindows 2.2.1 of National Instruments, for data acquisition, analysis and formation of a graphic interface. A general scheme of the system is depicted in FIG. 1, and FIGS. 2 and 3 are photographs of the exoskeleton. A portable version of the above system employing a portable laptop computer using a data acquisition card PC MCIA II (Model DAQ Card-700 of National Instruments) is depicted in FIGS. 4 and 5.

Though implementable in a transportable form, these instrumental monitoring systems of the neuro-psycho-physical condition remain extremely burdensome and require a time consuming preparation, including disposing and connecting the various components. It is a recurrently observed characteristic of reactive capabilities of an individual with a remarkably high degree of subordination to the emotional state of the person.

Referring to the case of a trivial blood pressure test, submission to a test of a neuro-psycho-physical condition may induce in a person an emotional state that markedly influences the results of the testing. Such an influence could be greatly reduced when not completely eliminated if the test could be completely and easily self-managed by the patient without requiring any preparatory work. Moreover, a frequent execution of the test, for example daily, would make it soon emotionally insignificant, thus enhancing the generation of more reliable data.

It is evident the interest and utility of a diagnostic method of the neuro-psycho-physical state of a person based on instrumentally generated data, implementable with a portable battery powered stand-alone instrument that does not require trimming or set-up operations and can be used at any moment of the day and practically in any place.

SUMMARY OF THE INVENTION

In view of the foregoing background, an object of the present invention is to fulfill the above described fundamental requirements.

It has been found that a multiparametric analysis of reaction times and of ergometric data in executing simple actions such as the pressing of a push button is greatly simplified and rendered far more reliable in terms of the results of the assessment by calculating the power that is exerted in executing the action of pressing a push button, as contemplated by the test.

Measurement of the power, intended in the present context, as the product of a force by a mean velocity or the product of the force by the distance covered by the moving finger within a certain time, has been demonstrated to be strictly correlated to the command process of the brain and of the nervous system.

In case of execution of an action of relatively small duration, such as the pressing of a push button, an instantaneous measurement of the power exerted may be obtained by instrumental measurements. Such a measure provides a good assessment of the way the brain command propagates through the neural and sensor circuits that control the execution of the required action. This implies a negligible physical effort, such as pressing a push button in a controlled manner.

In systems requiring actions to be developed in a relatively long span of time, the brain command does not appear to be determined instant by instant during the entire execution, but only in starting the action. Thereafter, the brain command is performed under a complex feedback control of the movement. In contrast, execution of an action of relatively brief duration, such as the pressing of a push button through a travel distance of few millimeters (to a mechanical stop), the ergometric data of the action and, in particular, the power exerted in substantial absence of feedback control, proves itself strongly tied to the brain command (i.e., reactivity).

Analysis of the data of these tests by a fuzzy logic microprocessor on the basis of a specific software is extremely simplified by a predetermination of the value of the exerted power in performing the action. The determination may be made by a simple logic circuitry. The calculated power value synthesizes optimally information on the speed of execution of the action and on the force exerted in performing it.

Moreover, by employing fuzzy logic processing there is no need to preestablish thresholds set by the doctor. This allows less rigid consequences in the overall result of the assessment. The whole monitoring system of the neuro-psycho-physical condition of a person may be contained in a device that can be easily handled with both hands or even with a single hand. The device may have a size and shape similar to those of a common remote control, cellular telephone or of a joystick.

Such a miniaturization of a battery powered system is extremely practical. Immediate use by the patient implies eventually a substantial disappearance of perturbed emotional states of the patient in performing the test after an initial period of daily use of the instrument.

The system according to the present invention for instrumentally monitoring of the neuro-psycho-physical condition of a person comprises a push button equipped with means for detecting the initial (start) instant of the pressing, and of the stopping instant when the push button is pushed against a mechanical stop equipped with a dynamometer or a strain gage providing a force signal. The system also includes an amplifier for the force signal of the dynamometer or strain gage, a pass band filter, and an analog/digital converter outputting a digital signal representative of the force exerted on the push button.

The system further includes a logic control and processing circuit of the start and stop signals and of the force signal for calculating on the basis of the length of the travel of the push button (which normally is a few millimeters) a digital value representative of the power exerted by the finger in pressing the push button. A fuzzy logic microprocessor performs a multiparametric evaluation of the time and ergometric values producing an index representative of the neuro-psycho-physical condition. A memory stores the processed data and/or the produced indexes, and includes interface circuits with the logic circuit and/or with the microprocessor. A display unit, an audio command generating unit, a keyboard or equivalent interface for start-up and selection of the type of test, and a battery is also included.

The system of the invention is entirely contained in an ergonomically shaped casing that may be handled using a single hand or with both hands. The casing may have the shape of a remote control or of a portable telephone or of a joystick, the latter being particularly suited to be handled with a single hand. A finger of which is used for exerting the pressing action of the push button.

In case the instrument of the invention is used for clinical purposes, such as monitoring the progress of the disease in a person having the Parkinson's disease, for example, the memory may record in a nonvolatile manner the data detected and elaborated during a certain number of tests. The memory may record repeatedly at regular (e.g., daily) intervals in a format not readable by the patient. The system may be connected to the data base of a medical center for downloading the acquired data in an appropriate coded format.

The visual interface of the instrument may be a liquid crystal display or any other alphanumeric and/or graphic display. The visual interface provides an interface of communication with the person during the test. The person is able to choose the specific test to be performed, and the visual interface illustrates this to the patient and, eventually for communicating the results of the tests in a quantitative or qualitative way, even by way of a number of predefined messages. Both the analysis software of the data as well as the communication messages with the patient or the person that undertakes and/or supervises the test, may be recorded in a nonvolatile manner, eventually modifiable by reprogramming the system's memory.

The acoustic interface may provide by itself or in cooperation with the display unit to the person doing the test preestablished alerting and start commands for executing the required actions. Optionally, the system may include a sensor for movement, such as an accelerometer, for example, for assessing the eventual presence when the hand tremors while holding the instrument, or of the person subjecting himself to the test and the frequency of the eventually present tremor.

Alternatively, instead of an accelerometer, the system may optionally include a subsystem of classification of movement employing an ON/OFF sensor. The sensor detects the tremor of the hand outputting an analog signal that is converted in a digital signal and is then stored. The conversion may be such that the bits 1 and 0 correspond to a closed and open condition of electrical contacts. Parameters representing the duration of the accelerations in the same direction and the number of transitions within a preestablished period of time may be fed to the fuzzy logic processing system.

Optionally, the system of the invention may also include a block of classification of the vocal articulation generating further parameters to be fed to the fuzzy logic processing system.

BRIEF DESCRIPTION OF THE DRAWINGS

FIGS. 1, 2 and 3 illustrate a bioengineering system for time and ergometric data acquisition according to the prior art.

FIGS. 4 and 5 illustrate another embodiment of the bioengineering system illustrated in FIGS. 1–3.

DETAILED DESCRIPTION OF THE PREFERRED EMBODIMENTS

Figure 6:
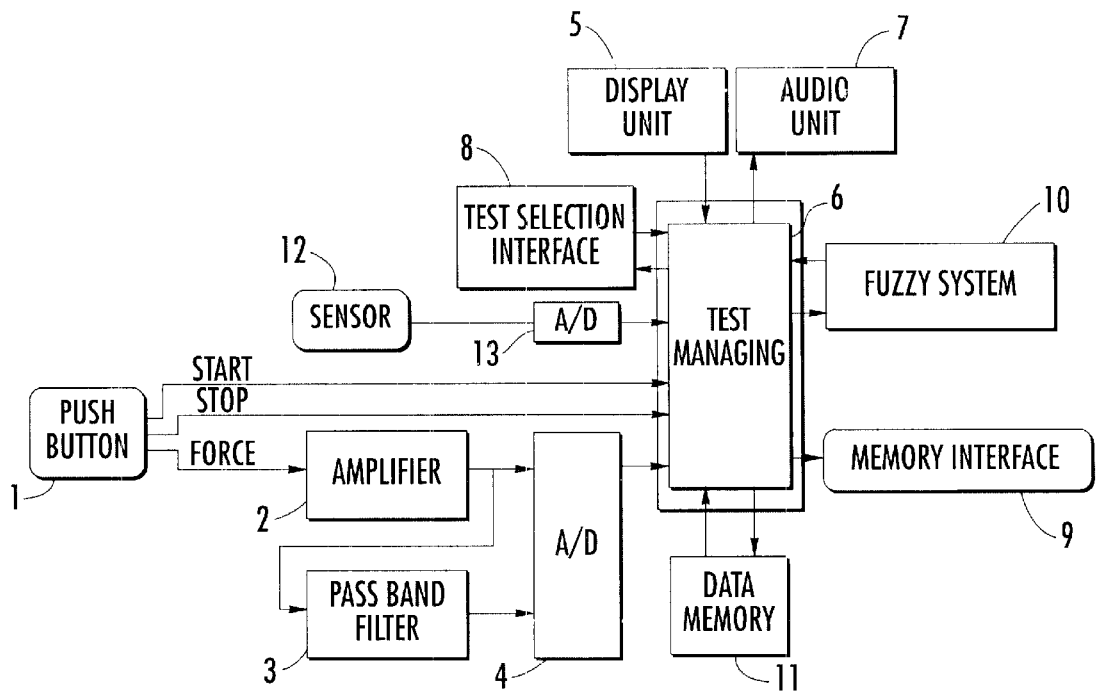
FIG. 6 is a block diagram of a system according to the present invention.

With reference to FIG. 6, the push button 1 of the instrument is provided with suitable devices for signaling the start instant of the depression of the push button, the instant when the travel of the push button ends, and for providing a signal representative of the force being exerted on the push button upon abutting against the mechanical stop. While the devices for providing the time information may be formed by simple electrical contacts that open and close an electrical circuit, the sensor of the force exerted may be a common strain gage of a dynamometer forming the mechanical stop against which the travel of the push button is stopped, or any functionally equivalent device.

The electrical signal provided by the strain gage or dynamometer is representative of the force being exerted and is amplified by an amplifier 2, filtered by a pass band filter 3, and converted by the analog/digital (A/D) converter 4. The (A/D) converter 4 provides a digital value to the input of the logic processing circuit 6 which receives, through other inputs, the time information in the form of a start instant of the pressure of the push button and of the end,signal of the travel of the push button. The functional block 8 is an interface for selection of the type of test which may be formed by a keyboard and/or by a directional scroll switch having a function similar to that of a mouse.

The display unit 5 may be a liquid crystal display or an array of LED indicators. The audio unit 7 may be a simple transducer capable of emitting a tone, such as an electronic bell or chime, or an audio playback system including a loudspeaker for emitting prerecorded messages and/or commands. A fuzzy logic processor 10 analyzes the results of the tests for generating an assessment of the neuro-psycho-physical condition as may be derived from the results of the tests on the basis of a preestablished software.

Through a communication interface 9, the system accesses a nonvolatile memory 11 which stores the test data and/or the results of the analysis performed by the fuzzy logic processor. The eventual presence of a motion sensor, typically an accelerometer 12, provides an indication of the presence of a tremor of the hand or hands of the person holding the instrument. Typically the sensor 12 provides an analog signal that is converted by an A/D converter 13. The digital data representative of the frequency of an eventual tremor of the hand or hands holding the instrument is fed to a dedicated input to the control logic circuit 6 that performs data handling and calculation.

Figure 7:
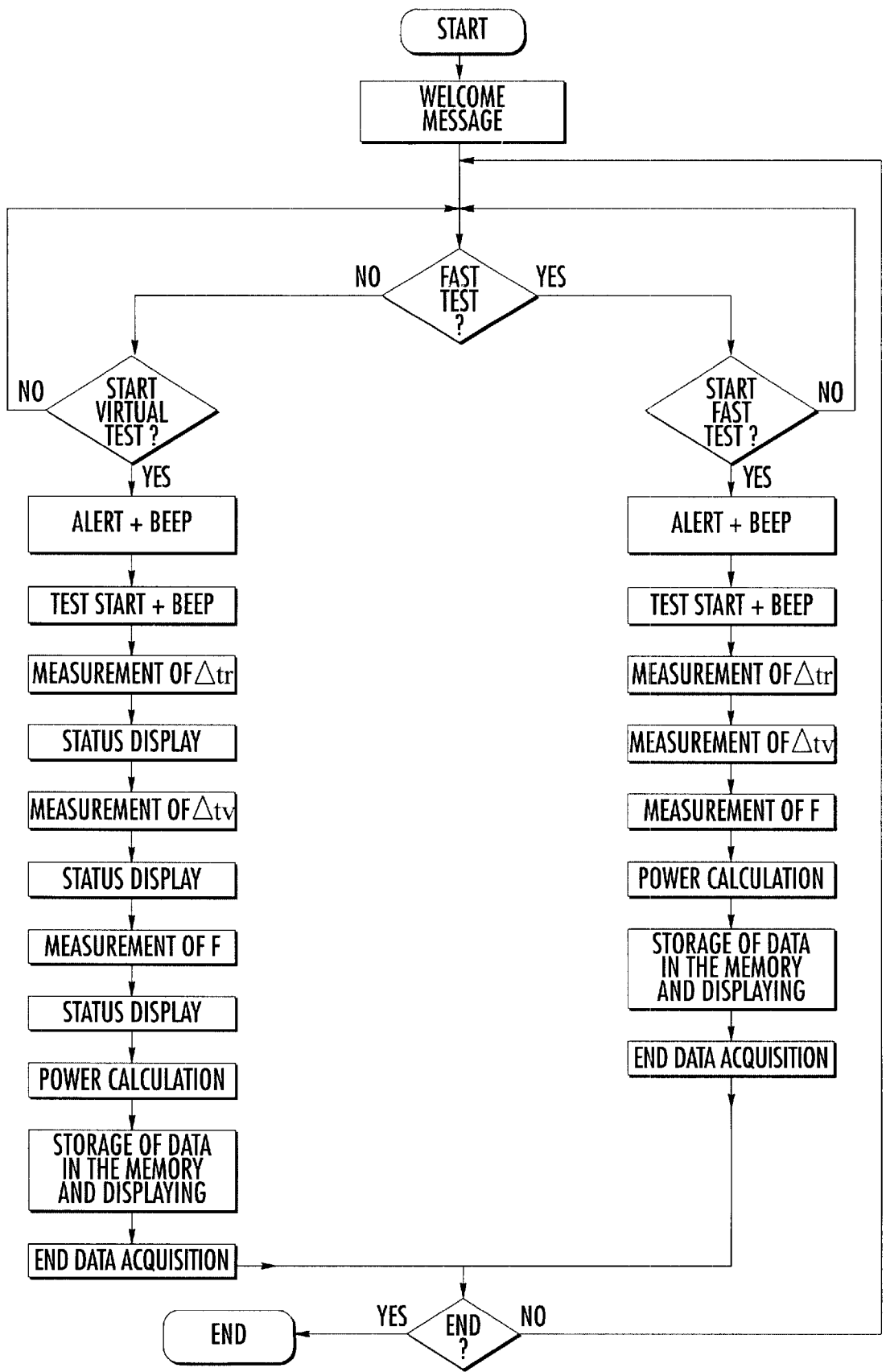
FIG. 7 is a flow chart of data acquisition, calculation and storing of the test data according to the present invention.

FIG. 7 is a flow chart of the data acquisition, calculation and storage of the test data according to an embodiment of the invention. As shown in the flow chart, the phase of data acquisition, calculation and storage of the test data may contemplate two types of tests. A first type is called a virtual test, in which the phases of alerting, commanding and execution of the requested action are all visualized on the display. The other type of test is called a quick or fast test, and is entirely identical to the virtual test, but the person doing the test is prevented from visually following the various phases of the tests on the display.

It has been found that the ability to visually follow the phases of execution of the test has the effect of expanding the reaction and execution times as compared to the same tests repeated without being able to visually follow the phases of execution, either through figures or illumination of confirmation LEDs. Such an effect of expanding the time intervals is yet another parameter that is taken into consideration by the fuzzy logic processing. The effect becomes more evident with the progress of the disease in a patient with Parkinson's disease.

Generally, the results of a predefined number of virtual tests and of a certain number of quick tests are accumulated in the memory. Both may be on the order of about 10 tests repeated in a relatively fast succession while recording the relative data in the memory. Upon completing the established number of tests, the fuzzy logic processor 10 reads and analyzes the results producing a global assessment of the neuro-psycho-physical condition.

Figure 8:
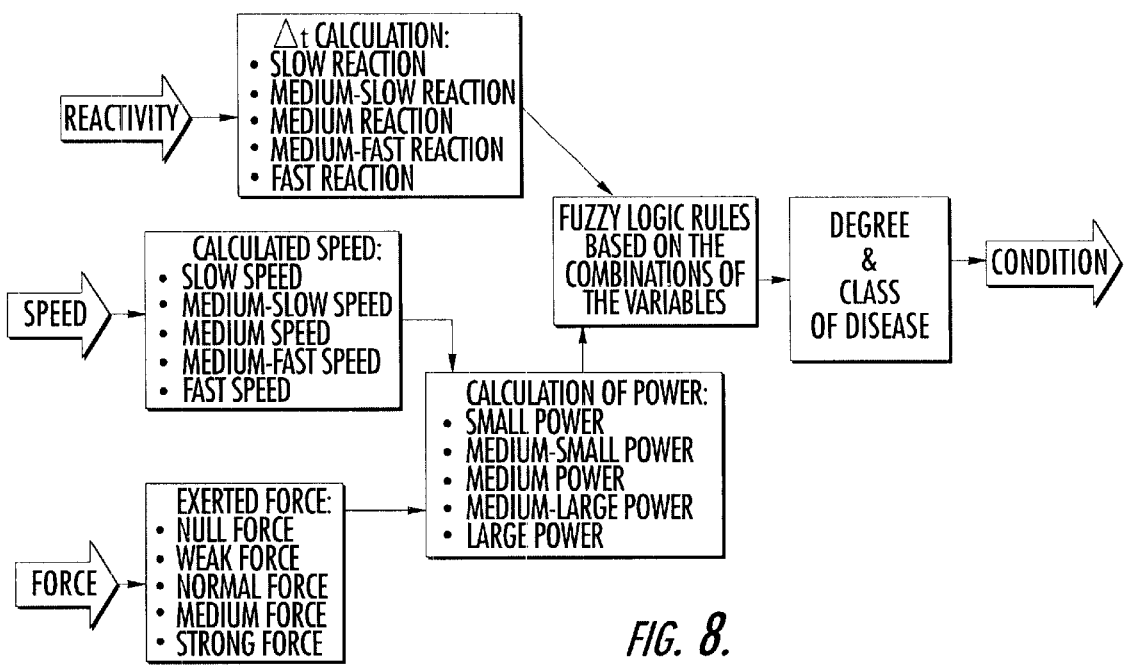
FIG. 8 shows the processing scheme implemented by the fuzzy logic microprocessor according to the present invention.

FIG. 8 describes a sample scheme of analysis of the test data by the fuzzy logic microprocessor 10 that generates an index of evaluation of the neuro-psycho-physical condition. In the example of FIG. 8, the optional detection and processing of the frequency of a tremor of the hand of the person holding the instrument is not included, but the fundamental parameters of reaction and execution times and of power exerted in performing the requested action are determined.

Figure 9:
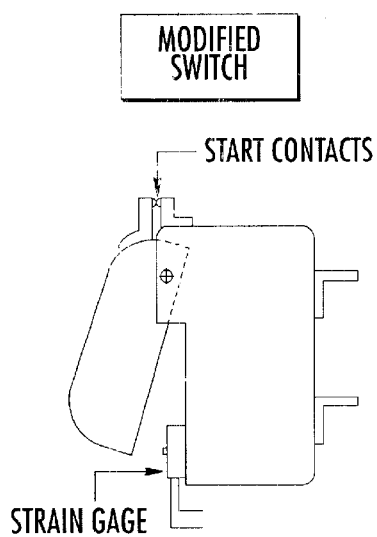
FIG. 9 shows a possible structure of a push button to be acted upon by the person subjected to the test according to the present invention.

FIG. 9 shows a possible structure of the push button 1 to be acted upon by the person doing the test. The start of the pressing action on the push button 1 is detected by a respective pair of electrical contacts suitably installed in a common push button switch. The stop signal at the end of the travel of the push button may be detected by the switch itself. The push button switch 1 is further adapted by installing a strain gage on the mechanical stop on which the push button abuts at the end of the travel.

Figure 10:
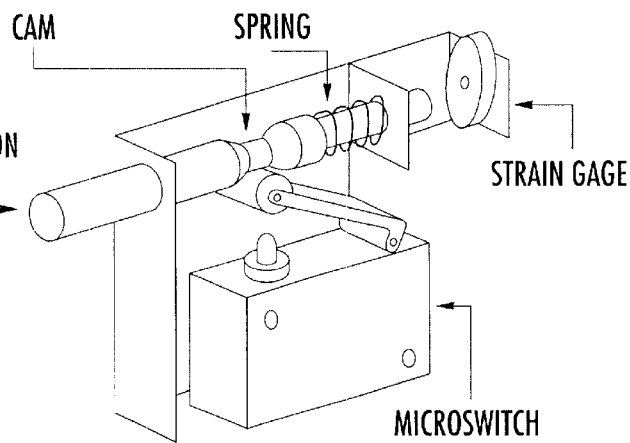
FIG. 10 shows an alternative structure of the push button illustrated in FIG. 9.

One of the test data used for calculating information on the power exerted is the speed with which the push button is moved from its rest position to the stop position, which may travel a few millimeters. The travel distance is generally between two and ten millimeters. It may be preferable to use a push button having a linear travel to obtain a more representative indication of the average speed of travel. In FIG. 10 an alternative structure of the push button is illustrated.

Figure 11:
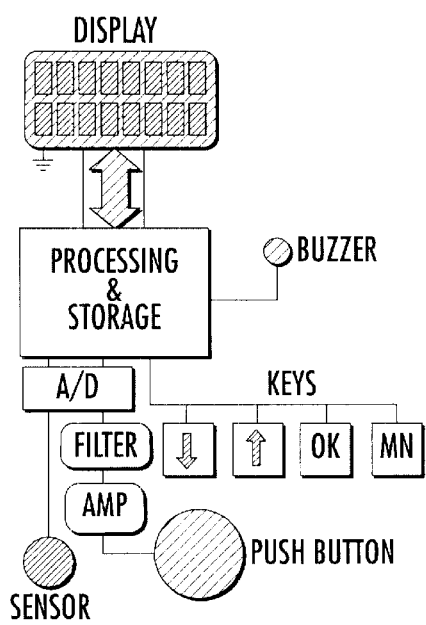
FIG. 11 shows an organizational scheme of the various parts that make up the portable system according to the present invention.

A scheme of the organization of the various parts that make up the system of the invention is depicted in FIG. 11. In the particular example shown, the selection interface has a minimum number of four keys, respectively used for recalling the menu (MN key), for scrolling through the menu in the desired direction (arrow keys) and for confirming the selection (OK key).

Figure 12:
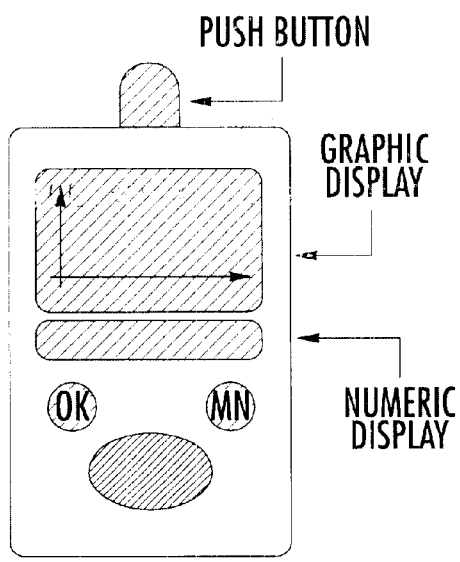
FIG. 12 shows a pocketable embodiment of the portable instrument according to the present invention.

The whole system is contained in a casing that can be handled with one or both hands, and which may have the shape and size of a common TV remote controller or cellular telephone, as graphically depicted in FIG. 12. The possibility of being handled with a single hand is a fundamental ergonomic aspect.

An objective of the present invention is to provide an interface between the person and the instrument that is the most acceptable as possible, and with a minimum emotional impact on the patient for daily monitoring his state of neuro-psycho-physical health. An instrument that can be handled and operated with a single hand as a common remote control reduces the psychological effect, and after a certain initial period of familiarization, the psychological effect becomes practically non-existent.

Figure 13:
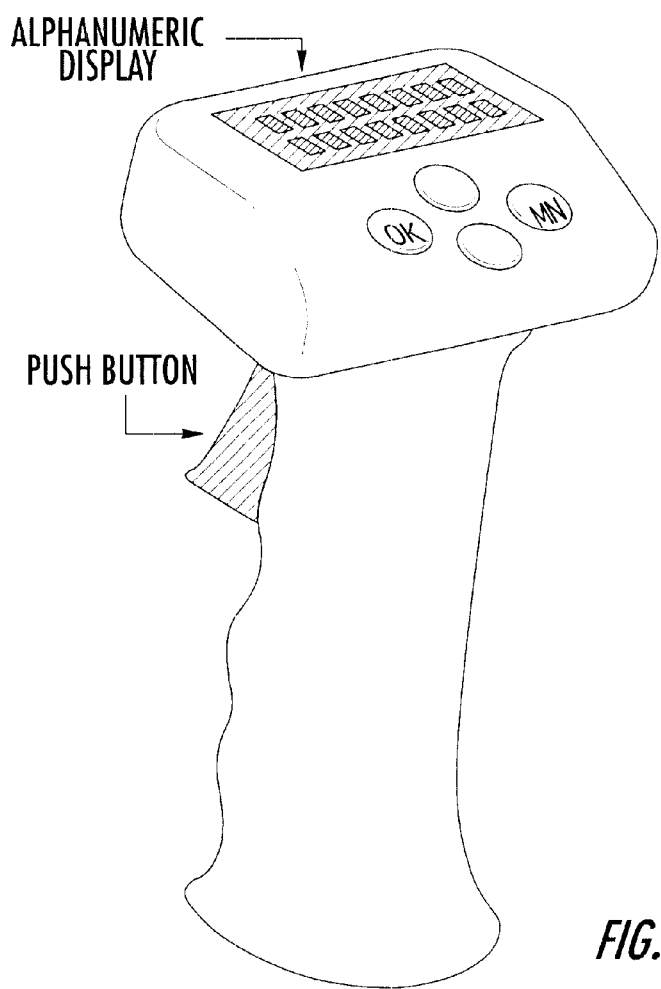
FIG. 13 shows an alternative embodiment of the portable system according to the present invention.

Another embodiment of the instrument having optimal ergonomic characteristics for being used with a single hand is depicted in FIG. 13. It corresponds to the shape of the joysticks used with electronic games. With reference to the figures, upon pressing the push button three signals are generally produced. A signal indicating start of the pressure, a stop signal at the end of the travel of the push button, and a signal indicating the force.

The microprocessor, after having commanded the issuance of an audio alerting signal starts a timer. After a small delay, the processor commands the emission of the audio start signal of the test, attributing the value of the timer to a first variable: start test tp. At the instant when the patient starts to press the push button, the relative start signal of the pressure causes the attribution of the current value of the timer to a second variable: start depression $t_i$. The control logic then determines the interval of time Dtp representing the reaction time:

$$\alpha tp_r = t_i - tp.$$

When the push button stops against the mechanical stop formed by the strain gage, the current value of the timer is attributed to a third variable: stop travel $t_f$. With the distance of travel by the push button being known, the control logic calculates the interval of time for traveling: $t_{if} = t_f - t_i$, and the average velocity of the push button is as follows:

$$v_m = \frac{\Delta x}{\Delta t} = \frac{x_f - x_i}{t_f - t_i} = \frac{corsa}{\Delta t_{if}}$$

Upon hitting the mechanical stop, the dynamometer or the strain gage provides a measure of the force with which the push button is being pressed against the mechanical stop. The force signal is amplified and before being converted to a digital value by the A/D converter, it is filtered through a pass-band filter to eliminate spurious readings that may be caused by eventual unbalances of the force sensor. The force data is multiplied by the data representing the average velocity producing a value that has the dimensions of power.

The fuzzy logic processor 10 generates information on the neuro-psycho-physical condition in a preestablished format, which, beside being nonvolatily stored in the memory, may be displayed on the display unit in an appropriate format that may also be preestablished by programming. The fuzzy logic processor 10 provides the information on the basis of the specific software stored in a program memory, and processes the power data together with the reaction time data for the various tests that have been performed The microprocessor compares the variables with a data base stored in the memory after having acquired the data of the tests from the memory. The microprocessor also generates data of global evaluation of the neuro-psycho-physical condition using a set of implications and fuzzy logic rules according to a specific software.

The instrument of the invention offers the possibility of maintaining a frequent and constant monitoring of the neuro-psycho-physical condition of a patient, allowing for a quick intervention in case anomalies are detected. The simplicity of use and the possibility of adapting the analysis software of the results of the tests to specific conditions to be revealed makes the system of the invention useful also for instrumentally verifying the state of alertness of car drivers.

The system, by suitably trimming and programming it, may be perfectly suitable to detect when a person is under the effects of alcohol as an alternative to the traditional blow-test and/or discriminate conditions of neuro-psycho-physical alterations due to the ingestion of alcoholics. Other conditions being detected may include excessive tiredness, jet-lag effects and effects that may be attributable to the consumption of drugs, and the like.

As already said above, the system of the invention may optionally classify an eventually present tremor of the hand holding the instrument, and/or classifying the vocal articulation of the person subjected to the test. The system then generates and provides additional parameters of evaluation to the fuzzy logic processor 10 according to appropriate processing algorithms.

Figure 14:
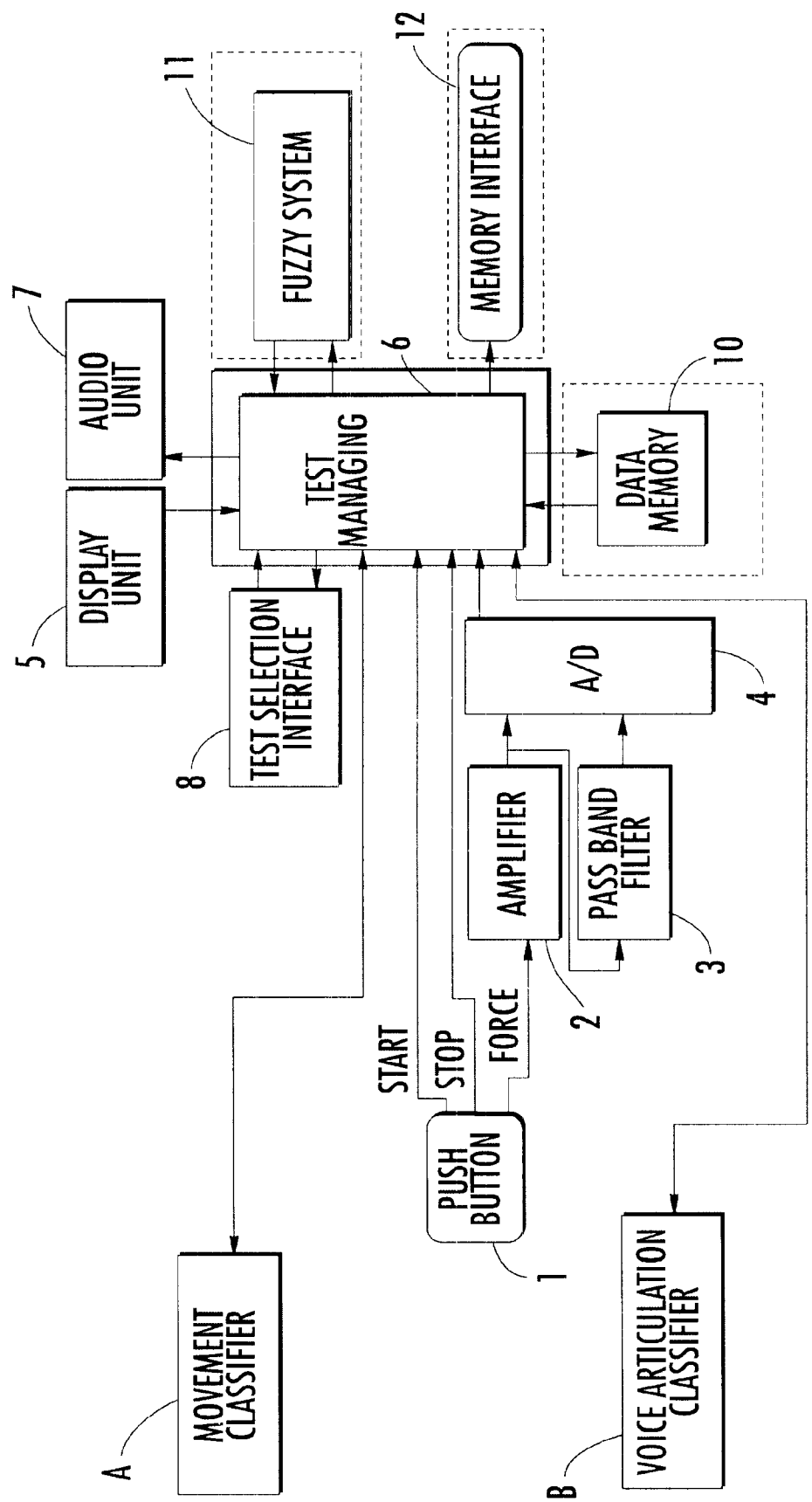
FIG. 14 shows a functional block diagram of the system with a movement classifier and with a vocal articulation classifier according to the present invention.

FIG. 14 is a functional block diagram of the system of the invention equipped also with a movement classifier A and with a vocal articulation classifier B which are evidenced in the figure by tracing them with thicker lines.

Figure 15:
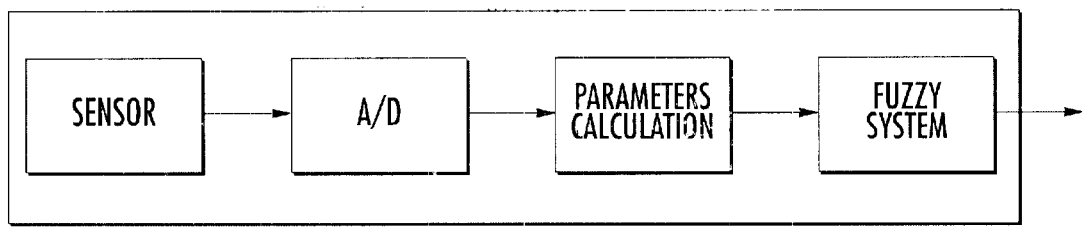
FIG. 15 is a functional diagram of the movement classifier of the scheme illustrated in FIG. 14.

BLOCK A (MOVEMENT CLASSIFIER). An architecture of the sub-system of movement classification is depicted in FIG. 15. The sensor may be an ON/OFF type accelerometer, and detects the tremor of the hand and outputs an analog signal that is converted to a digital signal by the A/D converter and is then stored. The analog signal may be converted to a digital signal in such a way that the bits 1 and 0 correspond to a closed and open condition of electrical contacts of the internal circuit of the ON/OFF sensor.

Two parameters: $N_{zero}$, and $N_{transition}$ are therefore generated by the processing logic circuitry of the block 6 of the scheme of FIG. 14. It is experimentally verified that there is a relation between these two parameters and the type of movement corresponding to them. If the person is calm and resting, the two parameters are both null or close to zero.

The $N_{zero}$ parameter represents the overall duration of acceleration phases within a certain period of time of monitoring and provides a measure of the intensity of the movement. For example, when making movements with the arm holding the instrument, the corresponding values of $N_{zero}$ increases. The $N_{transition}$ parameter represents the number of transitions ON/OFF that occur within the certain period of time of monitoring. Its value increases with the frequency of repeated sharp movements.

These two parameters are input to fuzzy logic processing algorithm of classification of the movement. On the basis of experimental measurements, the values that the two parameters $N_{zero}$ and $N_{transition}$ may take may be grouped in five fuzzy sets, for example, corresponding to the values Very Low, Low, Medium, High and Very High. Similarly, the evaluation of the tremor is established according to five fuzzy classes corresponding to Very Calm, Calm, Normal, Agitated and Very Agitated.

The fuzzy rules are defined by considering all possible cases. In all the rules, the antecedent contains both input parameters and all the possible combinations among the fuzzy sets of both parameters are contemplated. The rules are of the type as follows.

Figure 16:
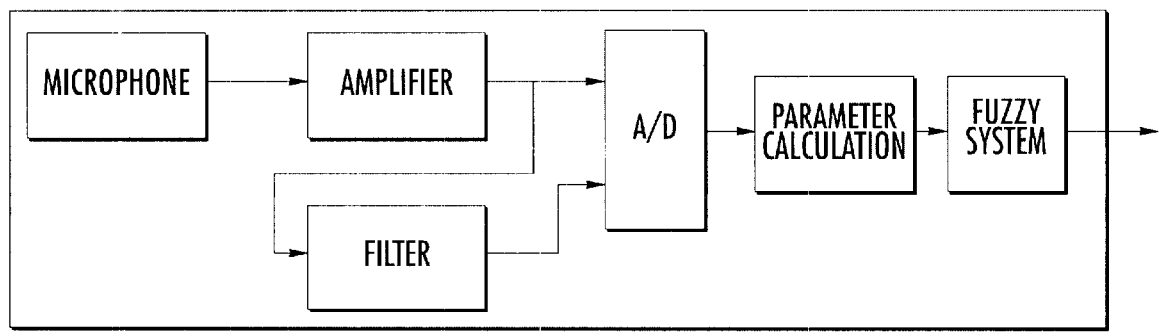
FIG. 16 is a functional diagram of the classifier for vocal articulation of the scheme illustrated in FIG. 14.

IF $N_{zero}$ IS Very Low AND $N_{transition}$ IS Very Low THEN tremor IS Very Calm IF $N_{zero}$ IS Low AND $N_{transition}$ IS Medium THEN tremor IS Calm IF $N_{zero}$ IS Medium AND $N_{transition}$ IS Low THEN tremor IS Normal BLOCK B (VOICE ARTICULATION CLASSIFIER). An architecture of the subsystem of classification of the vocal articulation block B of the scheme of FIG. 14 is depicted in FIG. 16. The voice signal is acquired by a microphone, amplified, filtered and fed to an A/D converter. The logic circuitry of the block 6 of the scheme of FIG. 14 calculates the parameters that are classified according to fuzzy logic processing rules.

By adding this function of vocal classification, the psychomotility reaction of the patient following a visual stimulation is measured. A so-called immediate reading test is carried out, whereby the patient must pronounce loudly a word immediately when it is visualized after a certain random delay from an alerting sound on a screen. In this way, it is not allowed any time for central cerebral processings, producing a read reaction.

In order to restrict the period of attention of the patient, an alerting audio signal precedes the visual stimulation. The delay from the displaying of the visual stimulation to the beginning instant of the vocal response of the patient represents the reaction time. It is also important to detect the duration of the response because it reflects the sequence of the various movements of vocal articulation under complex neural controls.

Figure 17:
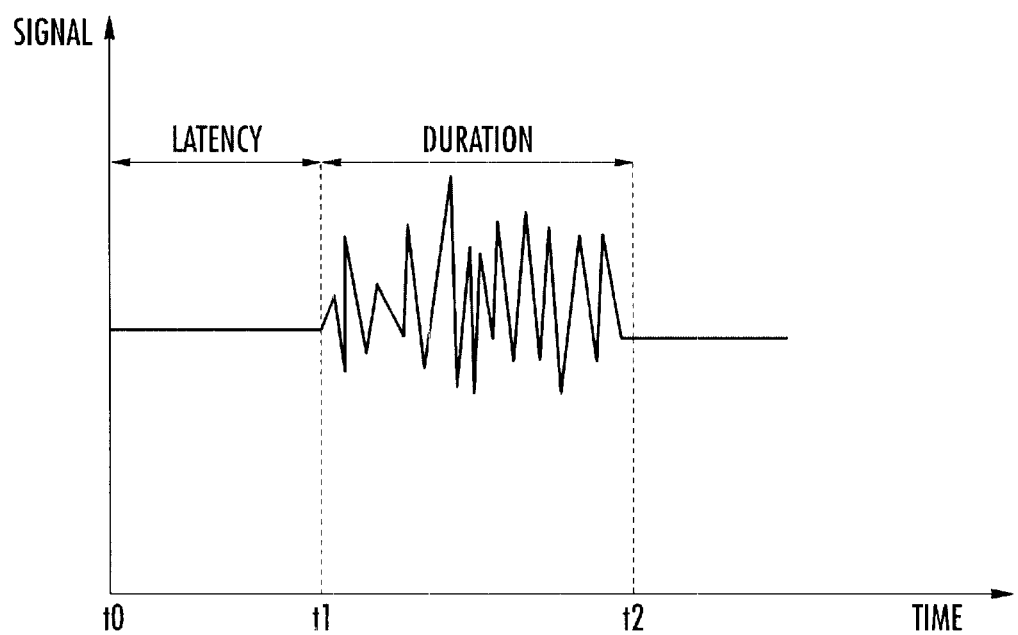
FIG. 17 is a diagram illustrating the acoustic levels of the noise and of the signal for the system according to the present invention.

An example of how this optional additional system of classification may be used is as follows. Before the push button test, a test of immediate reading is carried out thus detecting the reaction time and the duration of the vocal response. These parameters are determined on the basis of the audio signal detected by the microphone, establishing a certain threshold corresponding to the boundary between the audio level of the vocal signal and background noise, according to the diagram of FIG. 17.

At instant t0, the system issues an audio impulse as an alerting signal and soon after displays on the display the word to be pronounced and starts a timer. After having received the audio stimulation, the patient at the instant t1 will begin to pronounce the word read from the display and will terminate to pronounce it at the instant t2.

The parameters that are measured are the reaction time, corresponding to the delay between the displaying of the word to be pronounced and the beginning of the reply from the patient, and the duration of the reply, that is, the time the patient takes for pronouncing the word read from the display. Therefore, the time of reaction and the duration of the reply are given by $\Delta tr = t1-t0$, and $\Delta duration = t2-t1$.

Figure 18:
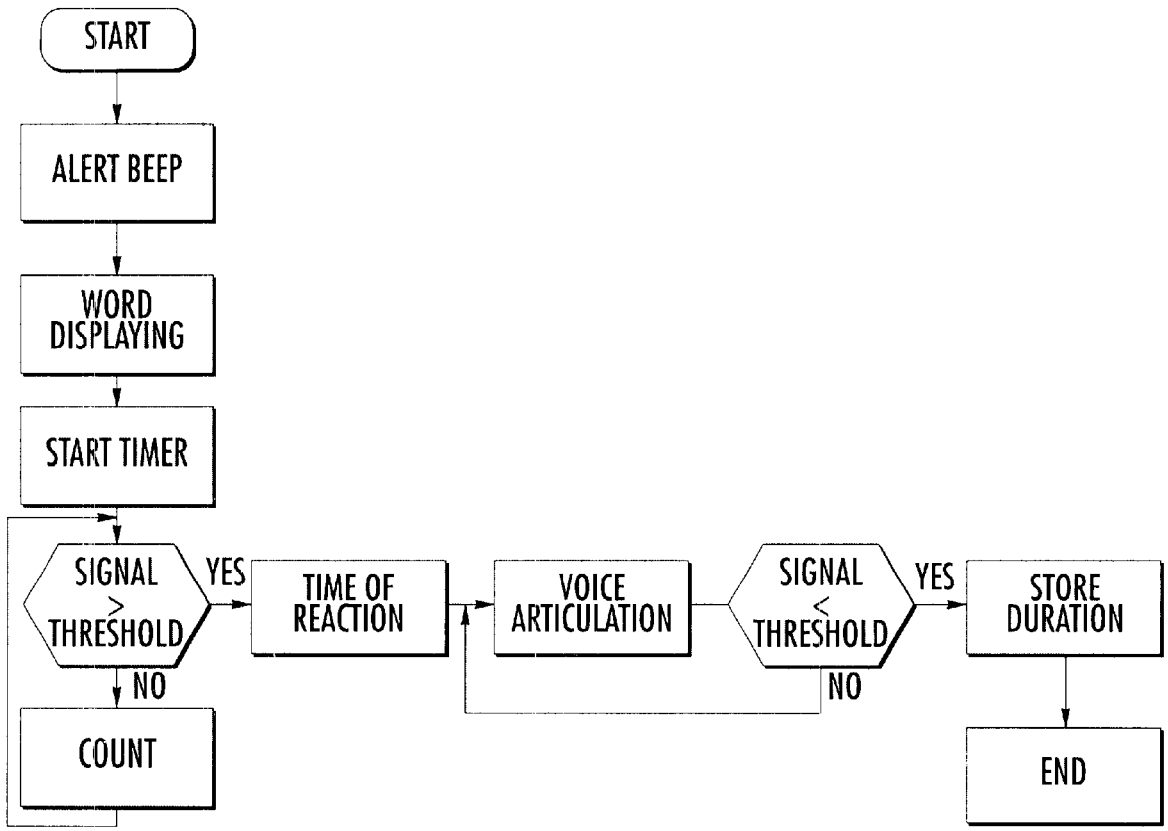
FIG. 18 is a flow chart for the management of the tests according to the present invention.

The management of this test is done by the block 6 of the scheme of FIG. 14 and may be illustrated by the flow chart of FIG. 18. On the basis of experimental measurements, the values that the parameters reaction time ($\Delta tr$) and duration of the reply ($\Delta duration$) may take, can be grouped in five fuzzy sets corresponding to the values Very Low, Low, Medium, High and Very High. Similarly, the articulation of the word may be classified according to five fuzzy classes corresponding to Very Difficult, Difficult, Normal, Fast and Very Fast.

The fuzzy rules are defined by considering all the possible cases. In all the rules, the antecedent contains both input parameters and all the possible combinations between the fuzzy sets of both parameters are considered. The rules are of the following kind:

IF $\Delta tr$ IS Low AND $\Delta duration$ IS Low THEN Word Articulation IS Difficult IF $\Delta tr$ IS Medium AND $\Delta duration$ IS Medium THEN Word Articulation IS Normal According to a preferred diagnostic scheme, once this test of vocal articulation terminates, an alerting signal is given to the patient that the test of the pressure of the push button is about to begin. In the interval of time that precedes the signal of initial pressing, the movement sensor detects the tremor of the hand. The processing logic elaborates the $N_{zero}$ and $N_{transition}$ for storing their values in the data memory.

Figure 19:
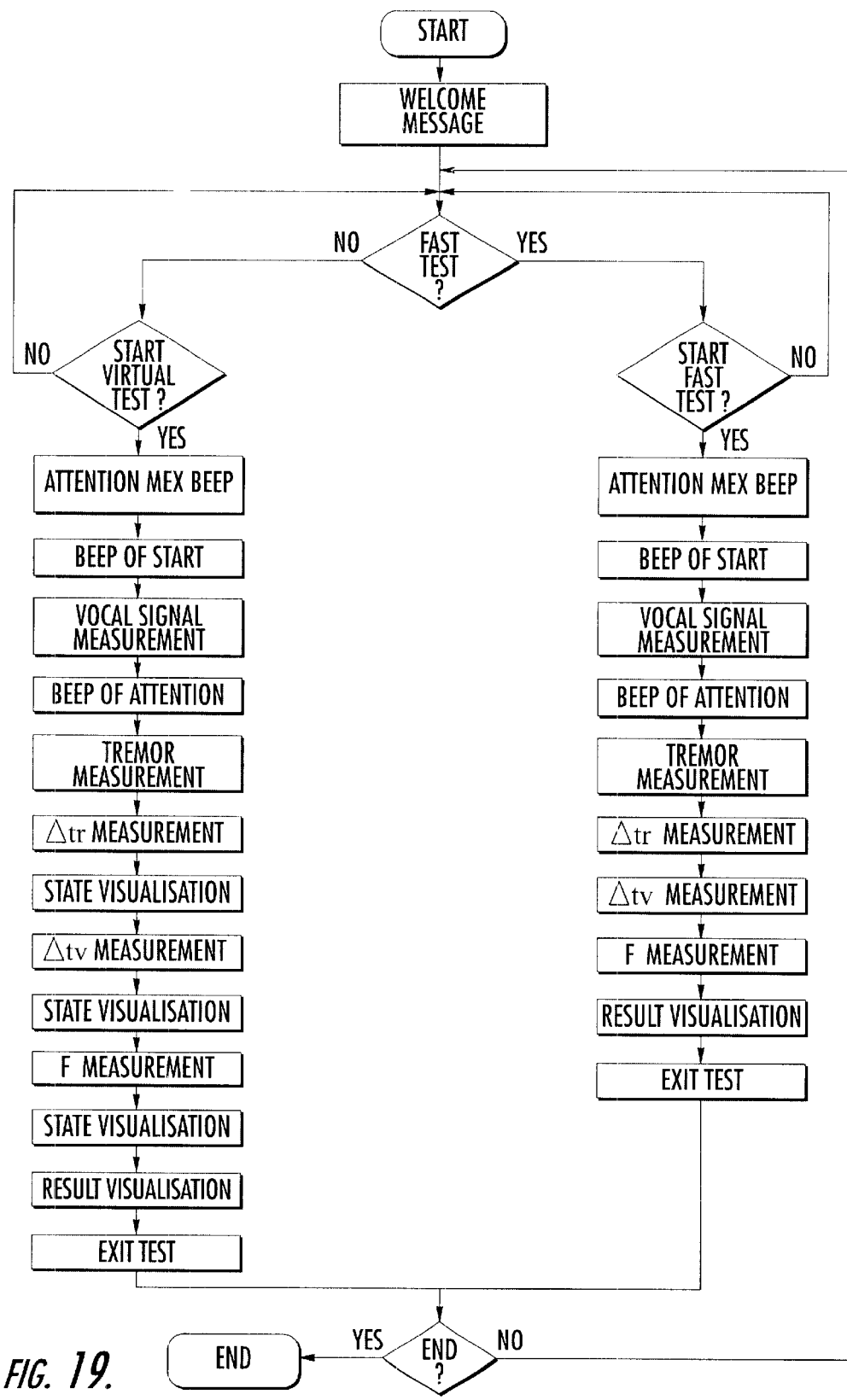
FIG. 19 is a further flow chart of the system according to the present invention.
Figure 20:
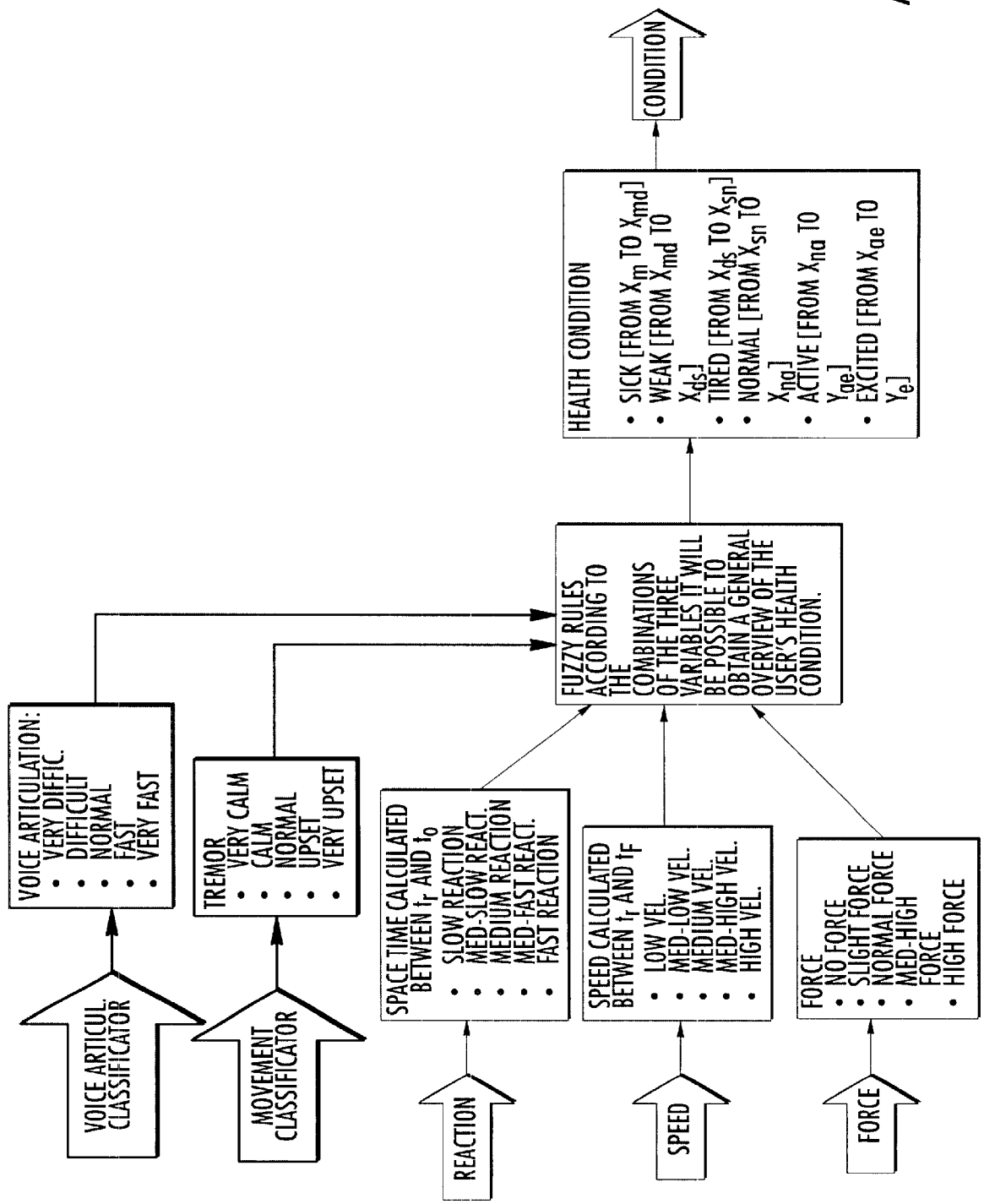
FIG. 20 is a scheme of the fuzzy logic assessment according to the present invention.

The managing program of the system may therefore be represented by the flow chart of FIG. 19. As far as the fuzzy logic evaluation is concerned, this processing may follow the scheme illustrated in FIG. 20. By virtue of its user-friendly characteristics, the instrument of the invention is suitable even for general personal use. For example, it may be used for alerting particular pathologies that may imply neuro-mobility disturbances. Such as, for example, but not exclusively, Parkinson's disease.

In case of pathological conditions, the instrument of the invention may contribute to improve patient-doctor relationship by allowing the doctor to analyze objectively and reliably data even in real time, or coming from several patients, without the need of frequent visits for controlling the conditions of his patients.

That which is claimed is:

1. A method of assessing a neuro-psycho-physical condition of a person, the method comprising:

acquiring reaction times, execution times and ergometric data of actions performed by the person carrying out a test;

processing the reaction times, the execution times and the ergometric data for calculating power exerted by the person in performing each action; and producing information on the neuro-psycho-physical condition of the person based upon the reaction times and the power exerted in performing each action.

2. A method according to claim 1, wherein the actions comprise pressing a push button from a rest position to a stop position; wherein acquiring the reaction times comprises detecting a reaction time to a command for pressing the push button; and wherein acquiring the execution times is based upon pressing the push button from the rest position to the stop position.

3. A method according to claim 2, further comprising determining a force exerted against a mechanical stop of the push button; and wherein calculating the power exerted comprises calculating a length of travel of the push button.

4. A method according to claim 1, wherein producing information is based upon processing a fuzzy logic algorithm.

5. A method according to claim 1, wherein acquiring the reaction times, the execution times and the ergometric data of the actions is provided using instrumentation.

6. A method according to claim 1, wherein the actions comprise pressing a push button from a rest position to a stop position; wherein acquiring the reaction times, the execution times and the ergometric data of the actions is provided using instrumentation carried in a hand of the person; the method further comprising determining a frequency of tremor of the hand when holding the instrumentation.

7. A method according to claim 6, wherein the frequency of tremor is determined using a motion sensor; the method further comprising:

generating a first parameter representative of a duration of acceleration of the push button during an interval of a detection time; and generating a second parameter representative of a number of ON/OFF transitions of the motion sensor during the interval of detection time;

the first and second parameters forming data pairs to be input to a fuzzy logic algorithm for evaluation of movement of the push button.

8. A method according to claim 1, further comprising measuring a reaction time from a stimulation for the person to articulate a vocal reply and measuring a duration of the vocal reply; the method further comprising providing data pairs of measured values of the reaction time and of the duration of the vocal reply to a fuzzy logic algorithm for evaluation.

9. A method of assessing a neuro-psycho-physical condition of a person using a hand-held instrumentation system, the method comprising:

pressing a push button carried by the hand-held instrumentation system from a rest position to a stop position based upon a command;

acquiring reaction times, execution times and ergometric data of the person pressing the push button from the rest position to the stop position;

processing the reaction times, the execution times and the ergometric data for calculating power exerted by the person pressing the push button; and producing information on the neuro-psycho-physical condition of the person based upon the reaction times and the power exerted pressing the push button, the producing information being based upon processing a fuzzy logic algorithm.

10. A method according to claim 9, further comprising determining a force exerted against a mechanical stop of the push button; and wherein calculating the power exerted comprises calculating a length of travel of the push button.

11. A method according to claim 9, the method further comprising determining a frequency of tremor of a hand when holding the system.

12. A method according to claim 11, wherein the frequency of tremor is determined using a motion sensor; the method further comprising:
   generating a first parameter representative of a duration of acceleration of the push button during an interval of a detection time; and
   generating a second parameter representative of a number of ON/OFF transitions of the motion sensor during the interval of detection time;
   the first and second parameters forming data pairs to be input to a fuzzy logic algorithm for evaluation of movement of the push button.

13. A method according to claim 9, further comprising measuring a reaction time from a stimulation for the person to articulate a vocal reply and measuring a duration of the vocal reply; the method further comprising providing data pairs of measured values of the reaction time and of the duration of the vocal reply to a fuzzy logic algorithm for evaluation.

14. A system for monitoring a neuro-psycho-physical condition of a person as a function of measuring a reaction time to a stimulation for the person to press a push button from a rest position to a stop position and as a function of ergometric data on pressing the push button, the system comprising:
   a push button assembly comprising a push button and a mechanical stop adjacent thereto, said push button assembly for detecting start, stop and a length of travel of said push button when pressed by a finger of the person, and said mechanical stop for providing a force signal based upon said push button being pressed to the stop position;
   a test management circuit connected to said push button assembly for determining power exerted by the finger pressing said push button based upon the detected start, stop and the length of travel of said push button, and on the force signal;
   a fuzzy logic microprocessor connected to said test management circuit for generating information representative of the neuro-psycho-physical condition of the person based upon a multiparametric evaluation of the detected start, stop and the length of travel of said push button and on the ergometric data of pressing said push button;
   a memory connected to said test management circuit; and
   a display unit connected to said test management circuit.

15. A system according to claim 14, further comprising an audio unit connected to said test-management circuit.

16. A system according to claim 14, further comprising a test selection interface connected to said test management circuit for selecting a type of test to be performed.

17. A system according to claim 14, wherein said mechanical stop comprises at least one of a dynamometer and a strain gage.

18. A system according to claim 14, further comprising:
   an amplifier connected to said mechanical stop for amplifying the force signal;
   a pass-band filter connected to an output of said amplifier for filtering the force signal; and
   an analog-digital converter connected to an output of said amplifier and said pass-band filter for outputting a digital signal representative of the force exerted on said push button.

19. A system according to claim 14, when said push button has a linear travel when pressed.

20. A system according to claim 14, further comprising a case for housing the system, wherein said case is adapted to be carried by the person.

21. A system according to claim 20, wherein said case has a joystick shape adapted to be held with a single hand of the person.

22. A system according to claim 14, further comprising a motion sensor connected to said test management circuit for providing a signal thereto indicating a frequency of tremor of a hand of the person when holding the system.

23. A system according to claim 22, wherein said motion sensor comprises an ON/OFF sensor.

24. A system according to claim 22, wherein said test management circuit processes
   a first parameter representative of a duration of acceleration of said push button during an interval of a detection time; and
   a second parameter representative of a number of ON/OFF transitions of said motion sensor during the interval of detection time;
   the first and second parameters forming data pairs to be input to said fuzzy logic microprocessor to be used for evaluation of movement of said push button.

25. A system according to claim 14, further comprising a vocal articulation unit connected to said test management circuit for measuring a reaction time from a stimulation for the person to articulate a vocal reply and for measuring a duration of the vocal reply; said vocal articulation unit providing data pairs of measured values of the reaction time and of the duration of the vocal reply to said fuzzy logic microprocessor for evaluation.

26. A system according to claim 25, wherein said vocal articulation unit comprises:
   a microphone;
   an amplifier connected to said microphone;
   a pass-band filter connected to an output of said amplifier; and
   an analog/digital converter connected to an output of said pass-band filter for producing the data pairs of measured values.

27. A hand-held instrumentation system for monitoring a neuro-psycho-physical condition of a person, the system comprising:
   a push button assembly comprising a push button and a mechanical stop adjacent thereto, said push button assembly for detecting start, stop and a length of travel of said push button when pushed by a finger of the person, and said mechanical stop for providing a force signal based upon said push button being pressed to a stop position;
   a test management circuit connected to said push button assembly for determining power exerted by the finger pressing said push button based upon the detected start, stop and the length of travel of said push button and on the force signal;
   a motion sensor connected to said test management circuit for providing a signal to said test management circuit indicating a frequency of tremor of the hand of the person when holding the hand-held system;

a fuzzy logic microprocessor connected to said test management circuit for generating information representative of the neuro-psycho-physical condition of the person based upon evaluation of the detected start, stop and the length of travel of said push button and on ergometric data of pressing said push button; and a display unit connected to said test management circuit.

28. A hand-held instrumentation system according to claim 27, further comprising a memory connected to said test management circuit.

29. A hand-held instrumentation system according to claim 27, further comprising an audio unit connected to said test management circuit.

30. hand-held instrumentation system according to claim 27, further comprising a test selection interface connected to said test management circuit for selecting a type of test to be performed.

31. A hand-held instrumentation system according to claim 27, wherein said mechanical stop comprises at least one of a dynamometer and a strain gage.

32. A hand-held instrumentation system according to claim 27, further comprising:

an amplifier connected to said mechanical stop for amplifying the force signal;

a pass-band filter connected to an output of said amplifier for filtering the force signal; and an analog-digital converter connected to an output of said amplifier and said pass-band filter for outputting a digital signal representative of the force exerted on said push button.

33. A hand-held instrumentation system according to claim 27, when said push button has a linear travel when pressed.

34. A hand-held instrumentation system according to claim 27, further comprising a case for housing the system.

35. A hand-held instrumentation system according to claim 34, wherein said case has a joystick shape adapted to be held with a single hand of the person.

36. A hand-held instrumentation system according to claim 27, wherein said motion sensor comprises an ON/OFF sensor.

37. A hand-held instrumentation system according to claim 36, wherein said test management circuit processes a first parameter representative of a duration of acceleration of said push button during an interval of a detection time; and a second parameter representative of a number of ON/OFF transitions of said motion sensor during the interval of detection time;

the first and second parameters forming data pairs to be input to said fuzzy logic microprocessor to be used for evaluation of movement of said push button.

38. A hand-held instrumentation system according to claim 27, further comprising a vocal articulation unit connected to said test management circuit for measuring a reaction time from a stimulation for the person to articulate a vocal reply and for measuring a duration of the vocal reply; said vocal articulation unit providing data pairs of measured values of the reaction time and of the duration of the vocal reply to said fuzzy logic microprocessor for evaluation.

39. A hand-held instrumentation system according to claim 38, wherein said vocal articulation unit comprises:

a microphone;

an amplifier connected to said microphone;

a pass band filter connected to an output of said amplifier; and an analog/digital converter connected to an output of said pass-band filter for producing the data pairs of measured values.

* * * * *

UNITED STATES PATENT AND TRADEMARK OFFICE
CERTIFICATE OF CORRECTION

PATENT NO.    : 6,416,485 B1
DATED         : July 9, 2002
INVENTOR(S)   : Alberto Rovetta, Antonio Cuce', Marco Dalessandri, Davide Platania and Gian Guido Rizzotto It is certified that error appears in the above-identified patent and that said Letters Patent is hereby corrected as shown below:

Column 2,
Line 10, delete "del controllo cerebrate)" insert -- del controllo cerebrale) --

Column 3,
Line 32, delete "to the joints" insert -- to the joint --
Line 34, delete "probe provide a signal" insert -- probe provides a signal --
Line 39, delete "with a ISA/EISA" insert -- with an ISA/EISA --
Line 40, delete "and by a software" insert -- and by software --

Column 5,
Line 35, delete "having the Parkinson's disease," insert -- having Parkinson's disease, --
Line 40, delete "to the data base of a " insert -- to the database of a --

Column 6,
Line 3, delete "converted in a digital signal" insert -- converted into a digital signal --

Column 7,
Line 5, delete "common strain gage of a" insert -- common strain gauge of a --
Line 8, delete "the strain gage or" insert -- the strain gauge or --
Line 16, delete "end, signal of" insert -- end signal of --

Column 8,
Line 20, delete "strain gage on the" insert -- strain gauge on the --

Column 9,
Line 5, delete " $\alpha t p_i = t_i - tp$ " insert -- $\Delta t p_i = t_i - tp$ --

Line 8, delete "strain gage, the current" insert -- strain gauge, the current --
Line 19, delete "strain gage provides" insert -- strain gauge provides --
Line 29, delete "which, beside being" insert -- which, besides being --
Line 36, delete "with a data base stored" insert -- with a database stored --
Line 54, delete "ingestion of alcoholics." insert -- ingestion of alcohol. --

Column 10,
Line 26, delete "algorithm of classification" insert -- algorithm for classification --

Column 11,
Line 37, delete "IF Δtr IS Low AND Aduration IS Low" insert -- IF Δtr IS Low AND Δduration IS Low --
Line 39, delete "IF Δtr IS Medium AND Aduration IS Medium" insert -- IF Δtr IS Medium AND Δduration IS Medium --

UNITED STATES PATENT AND TRADEMARK OFFICE
CERTIFICATE OF CORRECTION

PATENT NO. : 6,416,485 B1
DATED : July 9, 2002
INVENTOR(S) : Alberto Rovetta, Antonio Cuce', Marco Dalessandri, Davide Platania and Gian Guido Rizzotto It is certified that error appears in the above-identified patent and that said Letters Patent is hereby corrected as shown below:

Column 13,
Line 61, delete "and a strain gage." insert -- and a strain gauge. --

Column 15,
Line 6, delete "data of pressing said" insert -- data of the action of pressing said --
Line 14, delete "30. hand-held instrumentation" insert -- 30. A hand-held instrumentation --
Line 20, delete "and a strain gage." insert -- and a strain gauge. --

Signed and Sealed this

Twenty-fourth Day of December, 2002

JAMES E. ROGAN
*Director of the United States Patent and Trademark Office*